United States Patent
Ma et al.

(10) Patent No.: US 9,702,749 B2
(45) Date of Patent: Jul. 11, 2017

(54) LIQUID SURFACE DETECTION METHOD AND DEVICE, AND IMMUNOASSAY ANALYZER

(71) Applicant: SHENZHEN MINDRAY BIO-MEDICAL ELECTRONICS CO., LTD., Shenzhen (CN)

(72) Inventors: Jie Ma, Shenzhen (CN); Yanwen Weng, Shenzhen (CN); Yueping Chen, Shenzhen (CN)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 0 days.

(21) Appl. No.: 14/885,869

(22) Filed: Oct. 16, 2015

(65) Prior Publication Data
US 2016/0061644 A1   Mar. 3, 2016

Related U.S. Application Data

(63) Continuation-in-part of application No. PCT/CN2013/084039, filed on Sep. 24, 2013.

(30) Foreign Application Priority Data

Apr. 16, 2013 (CN) .......................... 2013 1 0130821

(51) Int. Cl.
*G01F 23/26* (2006.01)
*G01F 23/22* (2006.01)
(Continued)

(52) U.S. Cl.
CPC .......... *G01F 23/263* (2013.01); *G01F 23/265* (2013.01); *G01F 23/266* (2013.01);
(Continued)

(58) Field of Classification Search
None
See application file for complete search history.

(56) References Cited

U.S. PATENT DOCUMENTS

| 4,970,468 A | * | 11/1990 | Ishizawa | G01F 23/263 324/662 |
| 5,304,347 A | * | 4/1994 | Mann | G01F 23/263 422/50 |
| 2004/0253146 A1 | * | 12/2004 | Shiba | G01N 35/00663 422/64 |

FOREIGN PATENT DOCUMENTS

| CN | 2588334 Y | 11/2003 |
| CN | 101004424 B | 7/2007 |

(Continued)

*Primary Examiner* — P. Kathryn Wright
(74) *Attorney, Agent, or Firm* — Kory D. Christensen; Polsinelli LLP

(57) ABSTRACT

Disclosed are liquid surface detection methods and devices, and immunoassay analyzers. By changing the power source input of a signal drive circuit, an effective voltage of a drive signal applied by the signal drive circuit on a liquid dispensing probe is a negative voltage, so that the liquid dispensing probe is protected as the cathode in an electrolytic cell formed between the liquid dispensing probe and the cleaning fluid, and is prevented from being corroded by the cleaning fluid and rusting. Moreover, the intrinsic detection flexibility and performance of the liquid surface detection device can be ensured, and the requirements on the material and process of the liquid dispensing probe are not high, thereby effectively controlling the cost.

8 Claims, 5 Drawing Sheets

(51) Int. Cl.
  *G01N 35/10*  (2006.01)
  *G01N 33/53*  (2006.01)
  *G01N 35/02*  (2006.01)

(52) U.S. Cl.
  CPC ....... *G01N 33/5302* (2013.01); *G01N 35/025* (2013.01); *G01N 35/1002* (2013.01); *G01N 35/1004* (2013.01); *G01N 35/1009* (2013.01); *G01N 2035/1025* (2013.01)

(56) References Cited

FOREIGN PATENT DOCUMENTS

| | | |
|---|---|---|
| CN | 201237520 Y | 5/2009 |
| CN | 101556180 A | 10/2009 |
| CN | 201476844 U | 5/2010 |
| CN | 201540140 U | 8/2010 |
| CN | 101858770 A | 10/2010 |
| CN | 201828301 U | 5/2011 |
| CN | 201983833 U | 9/2011 |
| EP | 1422502 A1 | 5/2004 |
| JP | 3-115929 * | 5/1991 |

* cited by examiner

LIQUID SURFACE DETECTION METHOD AND DEVICE, AND IMMUNOASSAY ANALYZER

CROSS-REFERENCE

This application is a continuation-in-part of Patent Cooperation Treaty Application No. PCT/CN2013/084039, filed Sep. 24, 2013, which is hereby incorporated by reference.

TECHNICAL FIELD

This disclosure relates to medical equipment, and particularly to liquid surface detection methods and devices, and immunoassay analyzers using the same.

BACKGROUND

An immunoassay analyzer is highly automatic, where its liquid surface detection device can automatically detect a sample so that the sample can be added into a test position. The liquid surface detection device can mainly include three parts: a signal analysis circuit, a sample probe and a fluidic system, where the fluidic system can connect with the sample probe. When the sample probe reaches a liquid surface of the sample, the signal analysis circuit can recognize a liquid surface signal, so that the sample can be drawn and discharged thereafter. Each time the sample probe completes an absorption-discharging operation, it cleans the sample probe to prevent contaminating the next sample. A method for cleaning the sample probe commonly used today may immerse the sample probe in a cleaning fluid for cleaning.

In a fully automatic immunoassay analyzer, the liquid surface may generally be detected through a capacitance liquid surface detection technology. At this point, the sample probe may be connected in the signal analysis circuit as a variable capacitor, in which case the sample probe can have different capacitances with respect to different liquid surfaces and the signal analysis circuit can monitor changes in the capacitance of the sample probe. When the sample probe reaches the liquid surface, its capacitance may have changed and the signal analysis circuit can accurately recognize the liquid surface signal and determine whether the sample probe reaches the liquid surface by detecting a phase change caused by the changes in the capacitance of the sample probe.

The existing liquid surface detection methods are simple and reliable and have high detection sensitivity. However, during the use of the automatic immunoassay analyzer, since the cleaning fluid for cleaning the sample probe has a high ion concentration, electrochemical reactions can occur between the cleaning fluid and the sample probe, and the sample probe may get corroded by the cleaning fluid and become rusted after several cleanings, thereby requiring frequent replacement of the sample probe.

Such electrochemical corrosion may be caused by the following reasons: when impure metal (or alloy) is immersed within an electrolyte solution, active metal may lose electrons and be oxidized, so that primary battery reactions may occur to cause the corrosion. According to a primary battery model, two conditions are required to cause the electrochemical corrosion: (1) a medium (such as the cleaning fluid above) having a high ion concentration and (2) metal material with low purity.

Therefore, based on the above-described analysis, the rusting problem of the sample probe can be solved in view of two aspects as follows. In a first aspect, the cleaning fluid can be replaced by another liquid with a low ion concentration. Deionized water, for example, can be used to clean the sample probe to remove electrically conductive material. In a second aspect, the sample probe with high metal purity can be adopted. Up to now, when the liquid surface is detected using the capacitance liquid surface detection technology, the rusting problem of the sample probe are addressed by the two aspects described above; that is, the cleaning fluid or the metal material for the sample probe is replaced. These two aspects have their own drawbacks, however. For instance, when the deionized water, which lacks strong detergency, is used for cleaning, the sample probe may not be cleaned enough, and some residual contamination may exist to affect the overall performance of the analyzer. On the other hand, when the sample probe is instead made by some special metal with high purity, such as Ti, the rusting problem can be overcome, but new problems about manufacture cost may arise because that metal is very expensive and hard to process.

Besides, the liquid surface can be detected by technologies other than the capacitance liquid surface detection technology. As an example, a radio frequency detection method can be used to detect the liquid surface. However, this technology is complicated in structure and easy to be interfered.

SUMMARY OF THIS DISCLOSURE

In one aspect, a liquid surface detection method using a liquid dispensing probe can be provided. The liquid dispensing probe can communicate with a fluidic path, where the fluidic path can be used for liquid delivery. The liquid dispensing probe may be configured to have changes in its own electrical characteristic when the liquid dispensing probe reaches a liquid surface. The detection method can include: applying a drive signal on the liquid dispensing probe by a signal drive circuit, where an effective voltage of the drive signal is smaller than or equal to a potential of the fluidic path; detecting the electrical characteristic of the liquid dispensing probe and outputting a liquid surface detection signal that varies with the electrical characteristic of the liquid dispensing probe by the signal drive circuit; and determining whether the liquid dispensing probe reaches the liquid surface according to the liquid surface detection signal.

In another aspect, a liquid surface detection method using a liquid dispensing probe can be provided. The liquid dispensing probe may be configured to have changes in its own electrical characteristic when the liquid dispensing probe reaches a liquid surface. The detection method can include: applying a drive signal on the liquid dispensing probe by a signal drive circuit, where an effective voltage of the drive signal is a negative voltage; detecting the electrical characteristic of the liquid dispensing probe and outputting a liquid surface detection signal that varies with the electrical characteristic of the liquid dispensing probe by the signal drive circuit; and determining whether the liquid dispensing probe reaches the liquid surface according to the liquid surface detection signal.

In still another aspect, a liquid surface detection device can be provided, which may include a liquid dispensing probe and a signal drive circuit. The liquid dispensing probe, of which one end may communicate with a fluidic path used for liquid delivery, may be configured to have changes in its own electrical characteristic when the liquid dispensing probe reaches a liquid surface. The signal drive circuit can include a first power input port coupled to a first potential and a second power input port coupled to a second potential. The signal drive circuit can connect with the liquid dispensing probe to apply a drive signal on the liquid dispensing probe, so that the signal drive circuit can detect electrical characteristic of the liquid dispensing probe and output a liquid surface detection signal that varies with the electrical characteristic of the liquid dispensing probe. The first potential and the second potential can be configured by the signal drive circuit to provide the drive signal having an effective voltage that is lower than or equal to a potential of the fluidic path.

In yet another aspect, a liquid surface detection device can be provided, which may include a first power source supplying a first potential, a second power source supplying a second potential, a liquid dispensing probe and a signal drive circuit. The liquid dispensing probe may be configured to have changes in its own electrical characteristic when the liquid dispensing probe reaches a liquid surface. The signal drive circuit can include a first power input port coupled to the first power source and a second power input port coupled to the second power source. The first potential outputted by the first power source and the second potential outputted by the second power source can be configured by the signal drive circuit to generate a drive signal of which an effective voltage is a negative voltage. The signal drive circuit can also connect with the liquid dispensing probe to apply the drive signal on the liquid dispensing probe, so that the signal drive circuit can detect the electrical characteristic of the liquid dispensing probe and output a liquid surface detection signal that varies with the electrical characteristic of the liquid dispensing probe.

In some embodiments, the liquid dispensing probe can include an inner probe wall and an outer probe wall, where the outer probe wall can surround an external surface of the inner probe wall to form a capacitor structure together with the inner probe wall. One end of the inner probe wall can communicate to the fluidic path. The inner probe wall may also electrically connect with a drive signal output port of the signal drive circuit, and the outer probe wall may electrically connect with the signal drive circuit.

In some embodiments, the first power input port can be a high-electrical-level input port, and the second power input port can be a low-electrical-level input port.

In some embodiments, a positive voltage may be inputted to the first power input port, and a negative voltage may be inputted to the second power input port.

In some embodiments, the liquid surface detection device may further include a filtering circuit, an AD sampling circuit and a central control unit.

The filtering circuit can include an input port connecting with a signal output port of the signal drive circuit. The filtering circuit can receive the liquid surface detection signal outputted from the signal drive circuit, perform filtering processing on the liquid surface detection signal, and output the filtered liquid surface detection signal.

The AD sampling circuit can include an input port connecting with an output port of the filtering circuit. The AD sampling circuit can sample the filtered liquid surface detection signal from the filtering circuit, perform AD conversion on the filtered liquid surface detection signal, and obtain a digital liquid surface detection signal.

The central control unit can include an input port connecting with the AD sampling circuit. The central control unit can obtain the digital liquid surface detection signal, process the digital liquid surface detection signal, and determine whether the liquid dispensing probe reaches the liquid surface.

In still another aspect, an immunoassay analyzer can also be provided, where the immunoassay analyzer can include the above-described liquid surface detection devices. In some embodiments, the liquid dispensing probe can include a first liquid dispensing probe and a second liquid dispensing probe. The immunoassay analyzer can further include a master control system, a reaction wheel mechanism for holding one or more reaction cuvettes, a sample loading mechanism for providing one or more samples to be tested, a reagent loading mechanism for providing one or more reagents used during a test reaction in the one or more reaction cuvettes, a sample dispensing mechanism that uses the first liquid dispensing probe to draw the one or more samples from the sample loading mechanism, a reagent dispensing mechanism that uses the second liquid dispensing probe to draw the one or more reagents from the reagent loading mechanism, a cleaning mechanism for cleaning the first and the second liquid dispensing probes with cleaning fluid, and a fluidic path that communicates to the first and the second liquid dispensing probes for discharging the cleaning fluid after cleaning the first and the second liquid dispensing probes.

In the liquid surface detection methods and devices, and immunoassay analyzers of this disclosure, the effective voltage of the drive signal applied to the liquid dispensing probe can be smaller than or equal to the potential of the fluidic path, or can be a negative one. In this way, the liquid dispensing probe can be protected as a cathode to avoid corrosion and/or rusting within an electrolytic cell formed by the liquid dispensing probe and the cleaning fluid.

BRIEF DESCRIPTION OF THE DRAWINGS

The following detailed descriptions of respective embodiments in this disclosure can be understood better when combined with these figures, in which the same structure is represented by the same reference sign. In the figures.

DETAILED DESCRIPTION

Figure 1:
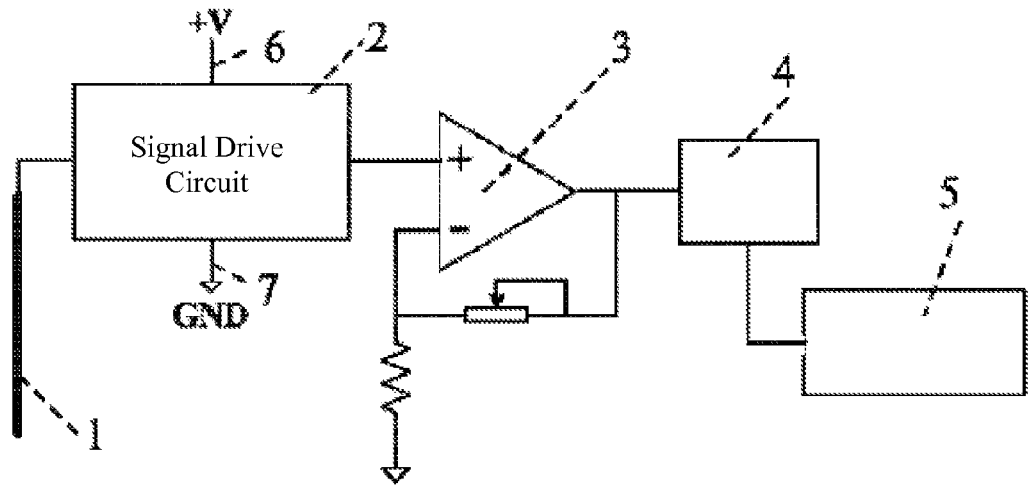
FIG. 1 is a structure diagram for a liquid surface detection device in the prior art.

Various embodiments of this disclosure are proposed using a capacitance liquid surface detection technology.

Liquid dispensing probes herein can be prevented from rusting through novel liquid surface detection methods and devices described below in this disclosure, which do not consider two necessary conditions for electrochemical corrosion, however.

It is found that an effective voltage of a drive signal applied to the liquid dispensing probe is a positive voltage during operation of an immunoassay analyzer. When the probe contacts for a long time a cleaning fluid that has a high ion concentration, the probe may be electrolyzed to lose electrons and thus get corroded. Due to this electrolytic reaction, the effective voltage of the drive signal applied to the liquid dispensing probe can be set as a negative voltage in this disclosure.

Immunoassay analyzers 100 can be provided in this disclosure, which can include a reaction wheel mechanism 11, a sample loading mechanism 12, a reagent loading mechanism 13, a sample dispensing mechanism 14, a reagent dispensing mechanism 15, a cleaning mechanism 16, a fluidic path 17, and a master control system 18. The master control system 18 can include a central control unit, and may operate to manage test procedures, calculate and/or analyze test results, and provide human-machine interaction interface. The reaction wheel mechanism 11 can include a reaction wheel 111 for holding one or more reaction cuvettes 112. The sample loading mechanism 12 that may include a sample wheel or a sample conveyor can operate to provide one or more samples to be tested. The sample dispensing mechanism 14 can include a first moving mechanism and a sample probe, where the sample probe can be fixed on the first moving mechanism. Under the control of the master control system 18, the first moving mechanism may bring the sample probe to draw the sample(s) from one or more sample containers on the sample wheel or the sample conveyor, and to add the drawn sample(s) into the reaction cuvette(s) 112. The reagent loading mechanism 13 that may include a reagent wheel can operate to provide reagent(s) used during test reactions. The reagent dispensing mechanism 15 can include a second moving mechanism and a reagent probe, where the reagent probe can be fixed on the second moving mechanism. Under the control of the master control system 18, the second moving mechanism may bring the reagent probe to draw the reagent from one or more reagent containers on the reagent wheel, and to add the drawn reagent into the reaction cuvette(s) 112. The cleaning mechanism 16 can operate to clean the sample probe and the reagent probe, so as to reduce contamination to a next dispensed liquid. The fluidic path 17 can communicate with the sample probe and the reagent probe, so as to discharge cleaning fluid after cleaning the sample probe and the reagent probe of liquid waste (such as unneeded sample, reagent, reaction fluid or cleaning fluid) drawn by the sample probe and/or reagent probe.

The immunoassay analyzer 100 may also include a liquid surface detection device since it is needed to detect a liquid surface within the sample container, the reagent container or the reaction cuvette 112 during operation. The liquid surface detection device can include a liquid dispensing probe and a signal drive circuit. The liquid dispensing probe can be configured to have changes in its own capacitance when the liquid dispensing probe reaches the liquid surface. The signal drive circuit can provide a drive signal to the liquid dispensing probe, detect the changes in the capacitance of the liquid dispensing probe, and output a liquid surface detection signal that may vary with the capacitance of the liquid dispensing probe. The liquid surface detection signal can be an analog electrical signal of which an amplitude value can vary with the capacitance of the liquid dispensing probe, where this analog electrical signal can be transmitted to the central control unit of the immunoassay analyzer after an analog/digital (A/D) conversion. Alternatively, the liquid surface detection signal can be an electrical level signal. In this case, when the capacitance of the liquid dispensing probe falls within a preset range, the signal drive circuit may output a low level; when the capacitance of the liquid dispensing probe exceeds the preset range, the signal drive circuit may output a high level. The electrical level signal can then be outputted to the central control unit. After receiving the liquid surface detection signal, the central control unit can determine whether the liquid dispensing probe has reached the liquid surface. In various embodiments, the liquid dispensing probe can be the sample probe and/or the reagent probe.

Various configurations of liquid surface detection devices are described when taking the sample probe as an example of the liquid dispensing probe.

Referring to FIG. 1, it is a structure diagram for a liquid surface detection device in the prior art, which can include a sample probe 1, a signal drive circuit 2, a signal filtering circuit 3, an AD sampling circuit 4 and a central control unit 5.

The sample probe 1 can be deemed as a part of the signal drive circuit 2, and it can affect an output signal of the signal drive circuit 2 in real time. The sample probe 1 is made of metal, and thus it can have an equivalent capacitance. When the sample probe 1 gets in touch with the liquid, its equivalent capacitance may change. At this point, the signal drive circuit 2 can convert the capacitance change into a voltage change as the output signal. Therefore, when the sample probe 1 reaches the liquid surface of a sample solution, the signal drive circuit 2 may have changes in its output signal.

The output signal of the signal drive circuit 2 can be processed by the signal filtering circuit 3, sampled by the AD sampling circuit 4 for A/D conversion, and then transmitted to the central control unit 5. The drive signal of the sample probe 1 may be provided by a first power input port 6 and a second power input port 7 of the signal drive circuit 2. In some cases, a positive voltage +V can be inputted to the first power input port 6, while a ground voltage GND can be inputted to the second power input port 7.

Figure 2:
FIG. 2 shows a waveform of a drive signal applied to a sample probe of the liquid surface detection device in FIG. 1.

Referring to FIG. 2, it shows a waveform of the drive signal applied to the sample probe 1 in FIG. 1. Here, the positive voltage +V and the ground voltage GND can be respectively applied to the first power input port 6 and the second power input port 7, and then the positive voltage +V and the ground voltage GND can be configured by the signal drive circuit 2 before being applied to the sample probe 1. In this case, an effective voltage of the drive signal applied to the sample probe 1 is a positive voltage. As described above, when the sample probe contacts for a long time the cleaning fluid that has a high ion concentration, it is because the effective voltage of the drive signal applied to the sample probe is a positive one, the sample probe will act as an anode in the electrolytic cell formed by the sample probe and the cleaning fluid, and the sample probe will be electrolyzed to lose electrons and get corroded.

Aiming at the above-described corrosion problem, immunoassay analyzers that can protect the sample probe from being corroded by the cleaning fluid are provided in this disclosure. In those immunoassay analyzers, in order to avoid corrosion and rusting, the sample probe may be protected as a cathode in the electrolytic cell formed by the sample probe and the cleaning fluid through increasing a potential of a complete fluidic path or setting the effective voltage of the drive signal applied to the sample probe as a negative voltage.

Figure 3:
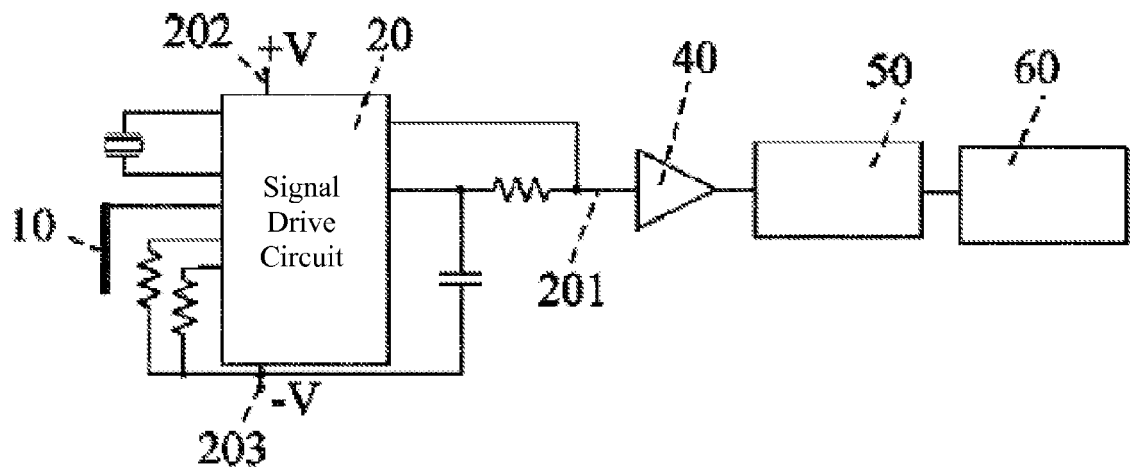
FIG. 3 is a structure diagram for a liquid surface detection device.
Figure 4:
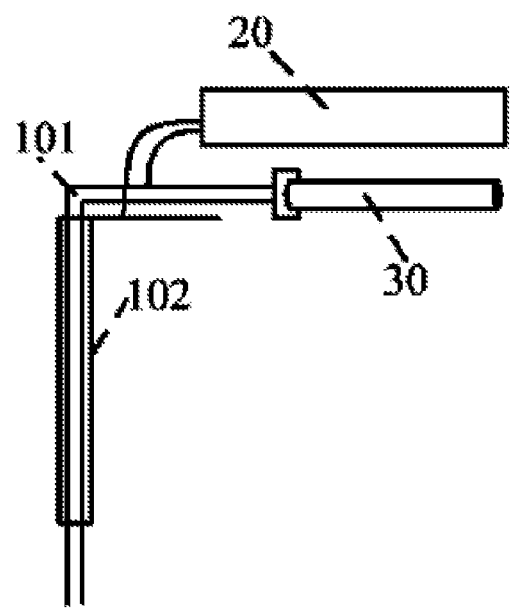
FIG. 4 is a structure diagram for a sample probe of the liquid surface detection device in FIG. 3.

FIGS. 3 and 4 are structure diagrams for a liquid surface detection device according to an embodiment of this disclosure. The liquid surface detection device can include a sample probe 10, a signal drive circuit 20, a fluidic path 30, a filtering circuit 40, an AD sampling circuit 50 and a central control unit 60.

The signal drive circuit 20 may connect with the sample probe 10. The signal drive circuit 20 can include a first power input port 202, a second power input port 203 and a signal output port 201, where a first potential and a second potential can be respectively applied to the first power input port 202 and the second power input port 203. In an example, the first potential is a high level, and the second potential is a low level correspondingly. After the signal drive circuit 20 configures the first potential and the second potential, these two potentials can be applied to the sample probe 10 as a drive signal. That is, the first potential and the second potential can be configured by the signal drive circuit 20 to obtain the drive signal to be applied to the sample probe 10. The fluidic path 30 can communicate to the sample probe 10 to deliver a cleaning fluid for cleaning the sample probe 10 and a sample solution drawn/discharged by the sample probe 10. In an embodiment, an effective voltage of the drive signal is smaller than or equal to a potential of the fluidic path 30. When the sample probe 10 is stretched into the sample solution to detect changes in a liquid surface of the sample solution, the signal drive circuit 20 can send out an output signal that may represent the changes of the liquid surface through the signal output port 201 according to the changes in the liquid surface of the sample solution detected by the sample probe 10. Here, since the effective voltage of the drive signal is smaller than or equal to the potential of the fluidic path 30, the sample probe 10 may be protected as a cathode in an electrolytic cell formed by the sample probe 10 and the cleaning fluid, so that the sample probe 10 can be prevented from corrosion and/or rusting by the cleaning fluid.

In most situations, the fluidic path 30 is connected to a water tank of the immunoassay analyzer 100, and thus the fluidic path 30 may be set to have a ground potential. For this reason, as long as the effective voltage of the drive signal is negative, the effective voltage of the drive signal can be ensured to be smaller than or equal to the potential of the fluidic path 30. In an example, a positive voltage +V can be inputted into the first power input port 202, a negative voltage −V can be inputted into the second power input port 203, and the drive signal obtained through configuring the positive voltage +V and the negative voltage −V by the signal drive circuit 20 can have a negative effective voltage. According to the capacitance liquid surface detection technique, the sample probe 10 may detect the changes in the liquid surface by affecting a charge-and-discharge time of the circuit. Therefore, although the effective voltage of the drive signal is a negative voltage, there is still a potential difference in the circuit to achieve the charge-and-discharge process. Correspondingly, the signal drive circuit 20 can still detect the changes in the capacitance of the sample probe 10.

Figure 5:
FIG. 5 shows a waveform of a drive signal applied to a sample probe of the liquid surface detection device in FIG. 3.

FIG. 5 shows a waveform for the drive signal applied to the sample probe 10 by the signal drive circuit 20, where this drive signal has a negative effective voltage when the positive voltage +V and the negative voltage −V are respectively applied to the first power input port 202 and the second power input port 203. The skilled person in the art can understand that, when different chips are used for driving in the signal drive circuit 20, the drive signal applied to the sample probe 10 can have a sawtooth waveform, a sinusoidal waveform, a square waveform or any other waveform. As long as the effective voltage of the drive signal is a negative voltage, the sample probe 10 can be protected as a cathode in the electrolytic cell formed by the sample probe 10 and the cleaning fluid no matter what the waveform is, so that the sample probe 10 can be prevented from corrosion and rusting by the cleaning fluid.

In an example, the sample probe 10 can include an inner probe wall 101 and an outer probe wall 102, where the inner probe wall 101 may connect with the signal drive circuit 20 and the fluidic path 30, and the outer probe wall 102 may connect with the signal drive circuit 20. The skilled person in the art can understand that, when the first power input port 202 and the second power input port 203 provide the sample probe 10 with the drive signal having the negative effective voltage, the inner probe wall 101 may act as a cathode while the outer probe wall 102 may act as an anode in the electrolytic cell formed by the inner probe wall 101, the outer probe wall 102 and the cleaning fluid. In this way, the inner probe wall 101 acting as the cathode can be protected from being corroded and/or rusted by the cleaning fluid. Although the outer probe wall 102 acts as the anode in the electrolytic cell, there is little chance for the outer probe wall 102 to be corroded and/or rusted since the outer probe wall 102 rarely contacts the cleaning fluid during the operation of the immunoassay analyzer 100.

The signal output port 201 of the signal drive circuit 20 can connect to the filtering circuit 40, which may perform filtering processing on the liquid surface detection signal outputted from the signal drive circuit 20 to filter out interference signals therein. The AD sampling circuit 50 that respectively connects with the filtering circuit 40 and the central control unit 60 can obtain the filtered liquid surface detection signal from the filtering circuit 40, perform A/D conversion on this signal to obtain a digital liquid surface detection signal, and transmit the digital signal to the central control unit 60. The central control unit 60 may analyze the digital signal to determine whether the liquid surface has been detected.

Figure 6:
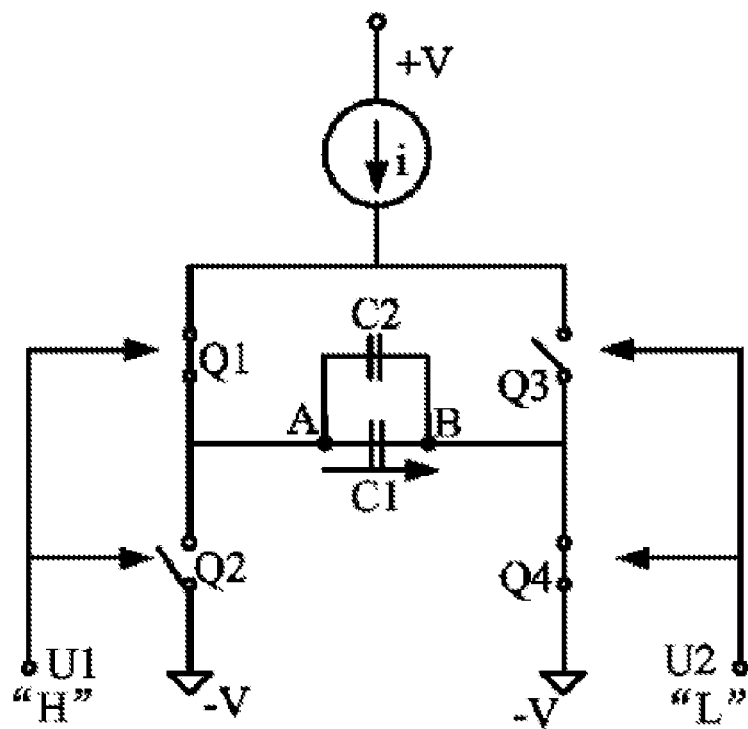
FIG. 6 is a schematic diagram illustrating a signal drive circuit when receiving a control signal.
Figure 7:
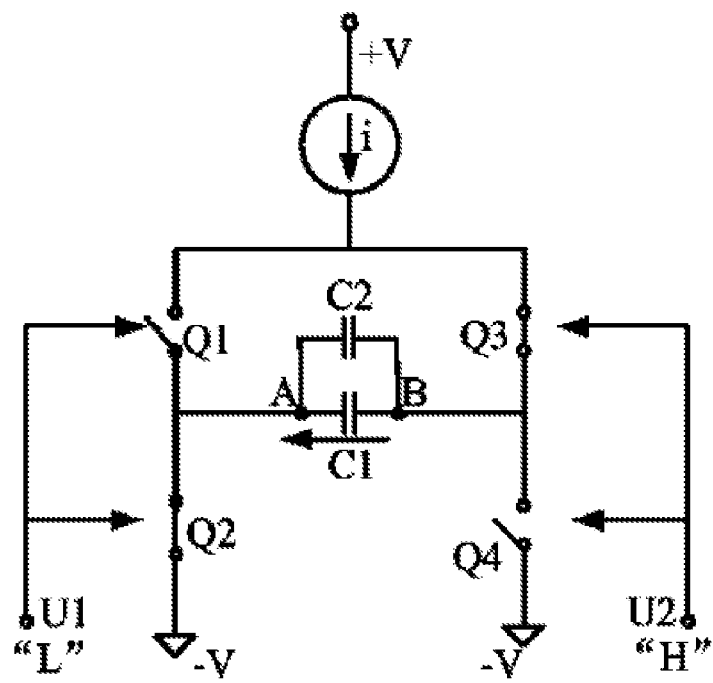
FIG. 7 is a schematic diagram illustrating a signal drive circuit when receiving another control signal.

In an embodiment, the signal drive circuit can be a multi-harmonic oscillator which generates oscillations by resistor-capacitor (RC) charge/discharge, and thus generates the drive signal for driving the sample probe. For convenience of understanding, circuit configurations of the signal drive circuit that correspond to the function of generating the required drive signal are described in this embodiment. Referring to FIGS. 6-7, circuit diagrams for the signal drive circuit are respectively shown in the two figures. The signal drive circuit can include a bridge circuit, a current source providing drive current and a first capacitor C1, where the bridge circuit may be formed by a first controllable switch Q1, a second controllable switch Q2, a third controllable switch Q3 and a fourth controllable switch Q4. The bridge circuit can include a first bridge arm and a second bridge arm, where the first bridge arm may be formed by the first controllable switch Q1 and the second controllable switch Q2, and the second bridge arm may be formed by the third controllable switch Q3 and the fourth controllable switch Q4. A node between the first controllable switch Q1 of the first bridge arm and the third controllable switch Q3 of the second bridge arm can be used as a high-level input port that couples to the first potential such as a positive voltage +V; another node between the second controllable switch Q2 of the first bridge arm and the fourth controllable switch Q4 of the second bridge arm can be used as a low-level input port that couples to the second potential such as a negative voltage −V. A power input port of the current source can be deemed as the first power input port that couples to the first potential, so that the node between the first and the third controllable switches Q1 and Q3 can couple to the first potential through the current source. Intermediate nodes of the first bridge arm and the second bridge arm can be configured as the output port of the signal drive circuit. The first capacitor C1 can further be connected between the intermediate nodes of the first bridge arm and the second bridge arm, and the inner probe wall of the sample probe can connect to either end of the first capacitor C1. During operation, the sample probe can be equivalent to a second capacitor C2 that is in parallel connection with the first capacitor C1. Control signals can be applied to respective control port of those four controllable switches Q1, Q2, Q3 and Q4, so that those four controllable switches Q1, Q2, Q3 and Q4 can be controlled by the control signals to have switchover between a switch-on state and a switch-off state. The control signals can include a first control signal U1 and a second control signal U2, where the first control signal U1 can be inputted to the control ports of the first controllable switch Q1 and the second controllable switch Q2, and the second control signal U2 can be inputted to the control ports of the third controllable switch Q3 and the fourth controllable switch Q4. The first control signal U1 and the second control signal U2 can be a high-level signal "H" or a low-level signal "L". The high-level signal and the low-level signal can be used for controlling the four controllable switches Q1, Q2, Q3 and Q4 to be switched on or off.

Figure 8:
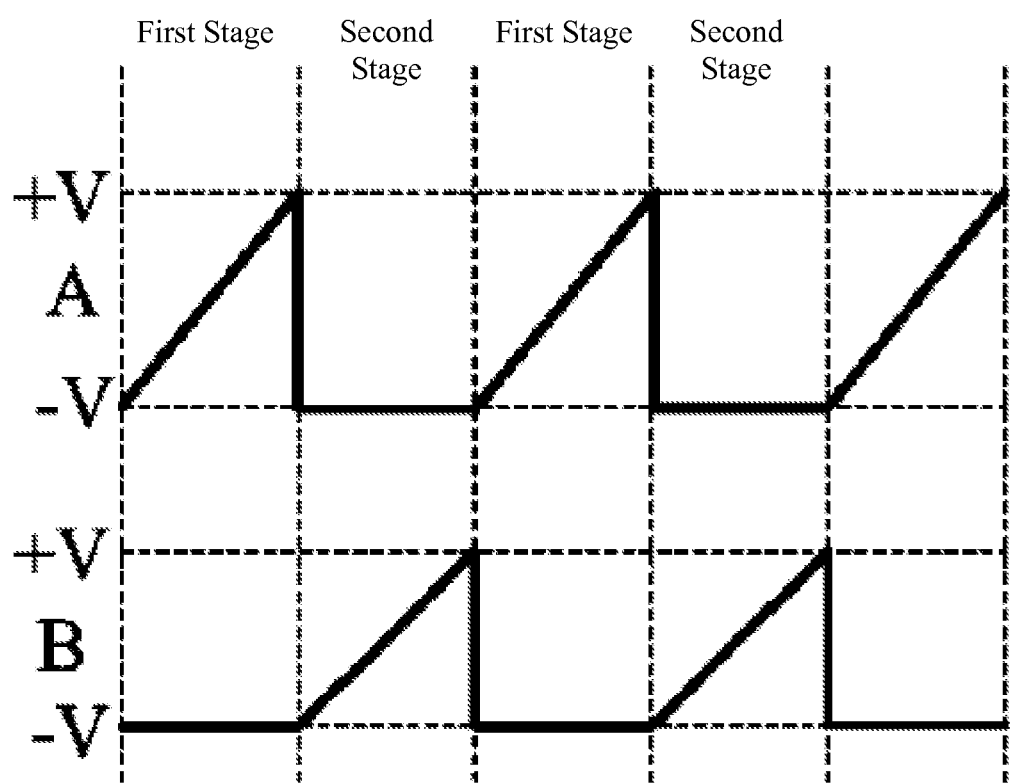
FIG. 8 shows signal waveforms for a capacitor C1 of a signal drive circuit when receiving different control signals.
Figure 9:
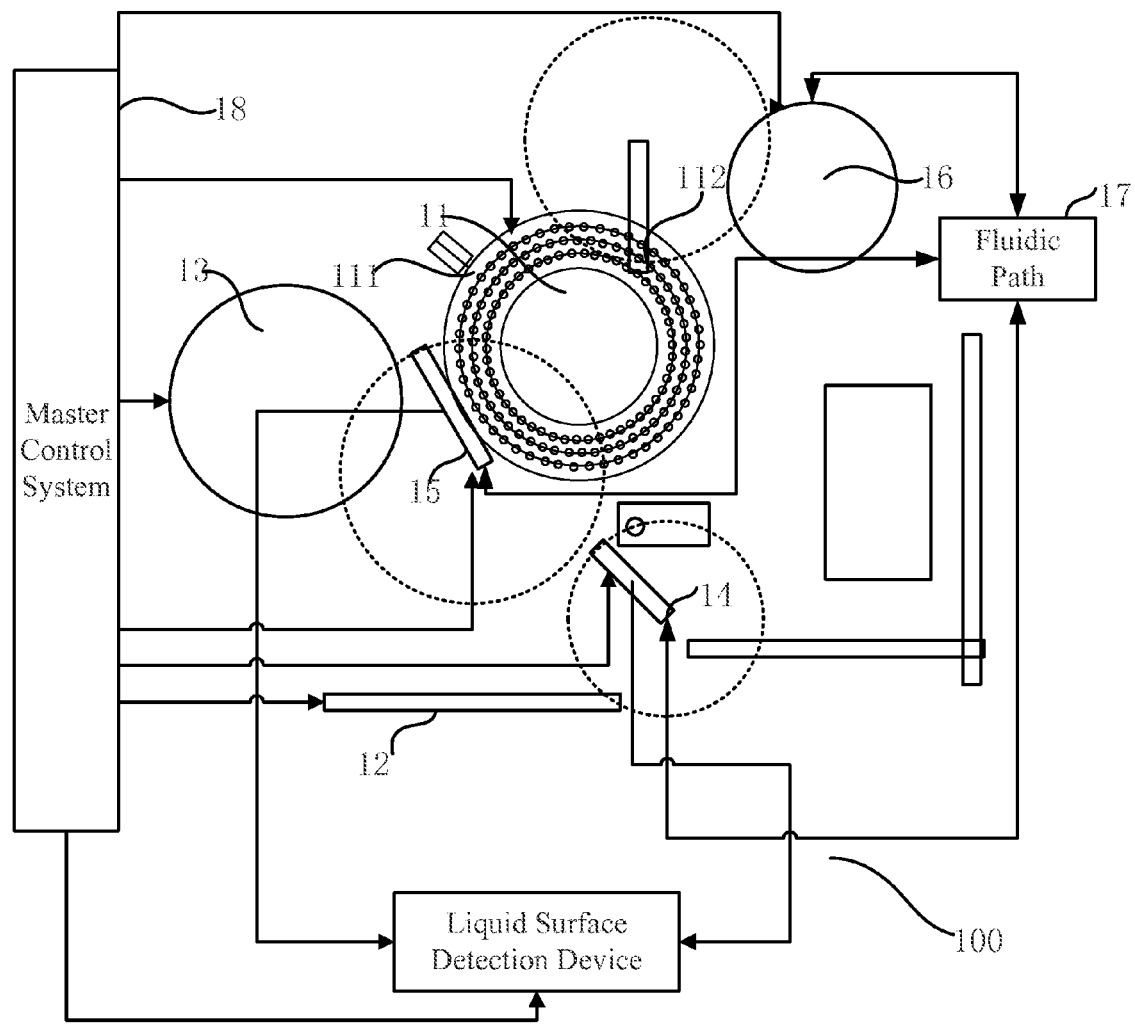
FIG. 9 is a schematic diagram for an immunoassay analyzer according to an embodiment of this disclosure, where the immunoassay analyzer includes the liquid surface detection device in FIG. 3.

Referring to FIG. 6, the first control signal U1 is a high-level signal "H", while the second control signal U2 is a low-level signal "L". In this case, the first controllable switch Q1 and the fourth controllable switch Q4 are switched on, and the second controllable switch Q2 and the third controllable switch Q3 are switched off Correspondingly, the current may flow from a point A to a point B in the circuit, so that voltage at the point A can gradually rise, and a negative potential −V can be obtained at the point B. A signal waveform for the first capacitor C1 under the control signal illustrated in FIG. 6 is shown by a first stage in FIG. 8.

Referring to FIG. 7, the first control signal U1 becomes a low-level signal "L", while the second control signal U2 becomes a high-level signal "H". In this case, the first controllable switch Q1 and the fourth controllable switch Q4 are switched off, and the second controllable switch Q2 and the third controllable switch Q3 are switched on. Correspondingly, the current may change to flow from the point B to the point A in the circuit, so that voltage at the point B can gradually rise, and a negative potential −V can be obtained at the point A. A signal waveform for the first capacitor C1 under the control signal illustrated in FIG. 7 is shown by a second stage in FIG. 8.

The equivalent capacitor C2 provided by the sample probe is one of the capacitors in the signal drive circuit, and the potential signals at both ends of the equivalent capacitor C2 are respectively consistent with those at the points A and B of the first capacitor C1. Therefore, according to internal configurations of the signal drive circuit, the effective voltage of the drive signal applied to the sample probe can be adjusted by regulating the voltages respectively inputted to the first power input port and the second power input port.

Additionally, when the signal drive circuit is implemented by a chip, an input power can be configured for the chip so as to adjust an effective value of the drive signal that is outputted from the chip to the sample probe. In various embodiments of this disclosure, the signal drive circuit can also be implemented through circuit designs for signal driving, where the drive voltage outputted by the signal drive circuit can be set as a negative voltage to be applied to the sample probe by adjusting its circuit configuration.

In the liquid surface detection devices provided in various embodiments of this disclosure, the first potential and the second potential can be configured so that the effective voltage of the drive signal can be smaller than or equal to the potential of the fluidic path. In some embodiments, the following configuration methods can be used to achieve the required effective voltage: modifying the first potential and the second potential that are applied to the first power input port and the second power input port; modifying partial circuit configurations of the signal drive circuit, such as resistance of resistor(s) and/or capacitance of capacitor(s), to obtain the drive signals with different effective voltages; or modifying parameter(s) of the chip(s) in the signal drive circuit to obtain the drive signal with the required effective voltage.

In another embodiment of this disclosure, another liquid surface detection device can be provided, which can include a first power source for providing a first potential, a second power source for providing a second potential, a liquid dispensing probe and a signal drive circuit. The liquid dispensing probe may be configured to have changes in its own capacitance when reaching a liquid surface. A first power input port of the signal drive circuit can couple to the first power source, and a second power input port of the signal drive circuit can couple to the second power source. The first potential outputted by the first power source and the second potential outputted by the second power source can be configured by the signal drive circuit, such that an effective voltage of a drive signal can be a negative voltage. The signal drive circuit can also connect with the liquid dispensing probe, such that the drive signal can be applied to the liquid dispensing probe, capacitance of the liquid dispensing probe can be detected, and a liquid surface detection signal that varies with the capacitance of the liquid dispensing probe can be outputted.

Compared with the existing circuit configurations in which the positive voltage and the ground signal are used as the power inputs for the first power input port and the second power input port, the liquid surface detection devices in various embodiments of this disclosure take positive and negative voltages as the power inputs; in this way, the effective voltage of the drive signal applied by the signal drive circuit on the sample probe can be a negative voltage, so that the sample probe can be protected as a cathode in the electrolytic cell formed by the sample probe and the cleaning fluid and can be prevented from being corroded and/or rusted by the cleaning fluid. Through this configuration, the liquid surface detection devices can also be ensured to have constant detection sensitivity and performance. Moreover, there is no high demand on the material and processing of the sample probe, thereby effectively controlling the cost.

The skilled persons in the art can understand that the liquid surface can also be detected based on changes in other electrical characteristics of the liquid dispensing probe besides the capacitance liquid surface detection technique by virtue of the liquid dispensing probe in the above described embodiments; for example, changes in resistance and/or inductance can be used to detect the liquid surface. Correspondingly, the liquid dispensing probes may be required to change to adapt for different liquid surface detection methods. The liquid surface detection devices can detect the changes in the electrical characteristic(s) of the liquid dispensing probe, and output the liquid surface detection signals that vary with the electrical characteristic(s).

According to above-described contents of this disclosure, the liquid surface detection devices can also be applied in equipment such as a biochemical analyzer that uses the liquid dispensing probe to detect the liquid surface.

This disclosure is described above as detailed illustrations with reference to specific implementations, while this disclosure should not be limited to these illustrations. For those of ordinary skills in the art, various conclusions or equivalents may be made without departing from the concept of this disclosure, while such conclusions or equivalents should be deemed to be included within the scope of this disclosure.

What is claimed is:

1. A liquid surface detection device, comprising:
   a first power source for supplying a first potential,
   a second power source for supplying a second potential,
   a liquid dispensing probe configured to have changes in its own electrical characteristic when the liquid dispensing probe reaches a liquid surface; and
   a signal drive circuit that comprises a first power input port coupled to the first power source and a second power input port coupled to the second power source; wherein the first potential outputted by the first power source and the second potential outputted by the second power source are configured by the signal drive circuit to generate a drive signal having a negative voltage as its effective voltage;
   wherein the signal drive circuit connects with the liquid dispensing probe, such that the signal drive circuit applies the drive signal to the liquid dispensing probe, detects the electrical characteristic of the liquid dispensing probe and outputs a liquid surface detection signal that varies with the electrical characteristic of the liquid dispensing probe,
   wherein the signal drive circuit further comprises a bridge circuit and a first capacitor, and the bridge circuit comprises a first bridge arm and a second bridge arm; the first bridge arm comprises a first positive node, a first intermediate node and a first negative node, and the second bridge arm comprises a second positive node, a second intermediate node and a second negative node; wherein the first capacitor are connected between the first and second intermediate nodes;
   the first and second positive nodes are connected with the first power input port to receive the first potential, and the first and second negative nodes are connected with the second power input port to receive the second potential; the first or second intermediate node is connected to the liquid dispensing probe to provide the drive signal to the liquid dispensing probe.

2. The liquid surface detection device of claim 1, further comprising:
   a filtering circuit comprising an input port connecting with a signal output port of the signal drive circuit; the filtering circuit receives the liquid surface detection signal outputted from the signal drive circuit, performs filtering processing on the liquid surface detection signal, and outputs the filtered liquid surface detection signal;
   an analog/digital (AD) sampling circuit comprising an input port connecting with an output port of the filtering circuit; the AD sampling circuit samples the filtered liquid surface detection signal from the filtering circuit, performs AD conversion on the filtered liquid surface detection signal, and obtains a digital liquid surface detection signal; and
   a central control unit comprising an input port connecting with the AD sampling circuit; the central control unit obtains the digital liquid surface detection signal, processes the digital liquid surface detection signal, and determines whether the liquid dispensing probe reaches the liquid surface.

3. The liquid surface detection device of claim 1, wherein the liquid dispensing probe comprises an inner probe wall and an outer probe wall; the outer probe wall surrounds an external surface of the inner probe wall to form a capacitor structure together with the inner probe wall;
   one end of the inner probe wall communicates to a fluidic path that is used for liquid delivery; the inner probe wall also electrically connects with a drive signal output port of the signal drive circuit, and the outer probe wall electrically connects with the signal drive circuit.

4. The liquid surface detection device of claim 1, wherein the first potential provides a positive voltage and the second potential provides a negative voltage.

5. The liquid surface detection device of claim 1, wherein the signal drive circuit is a multi-harmonic oscillator that generates oscillations to provide the drive signal to drive the liquid dispensing probe.

6. The liquid surface detection device of claim 1, wherein the first bridge arm comprises a first switch and a second switch, and the second bridge arm comprises a third switch and a fourth switch; the first switch is connected between the first positive node and the first intermediate node, the second switch is connected between the first intermediate node and the first negative node, the third switch is connected between the second positive node and the second intermediate node, and the fourth switch is connected between the second intermediate node and the second negative node;
   wherein when the first switch is switched on, the second and third switches are switched off and the fourth switch is switched on; and/or when the third switch is switched on, the first and fourth switches are switched off and the second switch is switched on.

7. The liquid surface detection device of claim 6, wherein the signal drive circuit generates a first control signal and a second control signal for switching on and off the first, second, third and fourth switches; the first control signal is inputted to the first and second switches, and the second control signal is inputted to the third and fourth switches.

8. The liquid surface detection device of claim 1, wherein the liquid dispensing probe is a sample probe for drawing and discharging a sample or a reagent probe for drawing and discharging one or more reagents.

* * * * *